(12) United States Patent
Bartosch

(10) Patent No.: US 11,779,227 B2
(45) Date of Patent: Oct. 10, 2023

(54) MULTISENSORY TECHNOLOGY FOR STRESS REDUCTION AND STRESS RESILIENCE

(71) Applicant: Kokon, Inc., New York, NY (US)

(72) Inventor: Veronika Bartosch, Demarest, NJ (US)

(*) Notice: Subject to any disclaimer, the term of this patent is extended or adjusted under 35 U.S.C. 154(b) by 660 days.

(21) Appl. No.: 16/489,092

(22) PCT Filed: Feb. 28, 2018

(86) PCT No.: PCT/US2018/020301
§ 371 (c)(1),
(2) Date: Aug. 27, 2019

(87) PCT Pub. No.: WO2018/160749
PCT Pub. Date: Sep. 7, 2018

(65) Prior Publication Data
US 2020/0000348 A1    Jan. 2, 2020

Related U.S. Application Data

(60) Provisional application No. 62/636,655, filed on Feb. 28, 2018, provisional application No. 62/464,824, filed on Feb. 28, 2017.

(51) Int. Cl.
*A61B 5/0205* (2006.01)
*A61M 21/02* (2006.01)
(Continued)

(52) U.S. Cl.
CPC .......... *A61B 5/02055* (2013.01); *A61B 5/021* (2013.01); *A61B 5/024* (2013.01);
(Continued)

(58) Field of Classification Search
CPC combination set(s) only.
See application file for complete search history.

(56) References Cited

U.S. PATENT DOCUMENTS

| 6,702,767 B1 | 3/2004 | Douglas et al. |
| 2004/0230252 A1 | 11/2004 | Kullok et al. |
| (Continued) | | |

OTHER PUBLICATIONS

International Search Report and The Written Opinion of the International Searching Authority, International Application No. PCT/US2018-020301, dated May 14, 2018.

*Primary Examiner* — Scott Luan
(74) *Attorney, Agent, or Firm* — Murtha Cullina LLP; Anthony P. Gangemi

(57) ABSTRACT

A multisensory environment apparatus for providing stress reduction to a user is disclosed. The apparatus includes a support frame that defines a recess. Auditory signal generators, somatosensory signal modules, olfactive signal modules, visual signal modules, and vestibular signal modules are positioned to deliver the associated to a user positioned in the recess. One or more of these signals are delivered to the user by the multisensory environment apparatus during a session. The delivery of the auditory and vibrotactile signals to the user work to meet the user's vital functions where they are, entrain them, and guide them to a more relaxed state, helping to reduce stress. The combination of the signals and the apparatus provide short term relief of acute stress, and long term benefits by breaking the cycle of chronic stress.

16 Claims, 5 Drawing Sheets

(51) Int. Cl.
   *A61B 5/024*   (2006.01)
   *A61B 5/11*    (2006.01)
   *A61B 5/021*   (2006.01)
   *A61B 5/369*   (2021.01)
   *A61M 21/00*   (2006.01)

(52) U.S. Cl.
   CPC ............... *A61B 5/11* (2013.01); *A61B 5/369* (2021.01); *A61M 21/02* (2013.01); *A61M 2021/0016* (2013.01); *A61M 2021/0022* (2013.01); *A61M 2021/0027* (2013.01); *A61M 2021/0044* (2013.01); *A61M 2205/3375* (2013.01); *A61M 2230/06* (2013.01); *A61M 2230/10* (2013.01); *A61M 2230/30* (2013.01); *A61M 2230/42* (2013.01); *A61M 2230/60* (2013.01); *A61M 2230/63* (2013.01); *A61M 2230/65* (2013.01)

(56) References Cited

U.S. PATENT DOCUMENTS

| | | |
|---|---|---|
| 2011/0004048 A1 | 1/2011 | Brunelle |
| 2011/0251535 A1 | 10/2011 | Bender |
| 2015/0313949 A1 | 11/2015 | Cutillo |
| 2016/0270656 A1 | 9/2016 | Samec et al. |
| 2017/0039045 A1 | 2/2017 | Abrahami et al. |
| 2017/0119994 A1* | 5/2017 | Argaman ............... A61M 21/00 |
| 2018/0292888 A1* | 10/2018 | Slepian ................. A61B 5/021 |

* cited by examiner

MULTISENSORY TECHNOLOGY FOR STRESS REDUCTION AND STRESS RESILIENCE

CROSS REFERENCE TO RELATED APPLICATION(S)

This application is a national stage patent application filing of International Patent Application No. PCT/US2018/020301, filed Feb. 28, 2018, which claims the benefit of U.S. Provisional Application Nos. 62/464,824, filed Feb. 28, 2017, and 62/636,655, filed Feb. 28, 2018, which are incorporated by reference as if disclosed herein in their entirety.

BACKGROUND

While stress and its associated symptoms are natural and occasionally useful, humans have always been susceptible to debilitating cycles of stress and anxiety. During the cycle, stressors result in physiological effects that prevent or impede an individual from performing certain steps, such as those that would eliminate the stressor, which in turn results in the production of yet more stress and associated physiological effects. Even when a stressor is removed, the physiological effects of the stressor can linger so as to impair an individual's ability to recognize and/or appropriately respond to the development of a new stressor.

Chronic stress and anxiety are also often left untreated. The lack of treatment is due to a variety of factors, such as the ever present nature of certain stressors and the speed at which new stressors can be delivered with advancements in technology. When treatment is administered, it can come in the form of a medication. However, the side-effects associated with such medications can be nearly as detrimental as the stressors themselves. Further, while these medications may allow the user to better cope with stressors, they may also be mood and personality altering, so that the user has difficulty being "themselves" during a course of treatment. Finally, the effectiveness of medication varies wildly from user to user. For some users, there is simply not enough benefit to offset the side-effects and cost often associated with a medicinal stress-reduction regimen.

SUMMARY

Some embodiments of the present disclosure include a multisensory environment apparatus for providing stress reduction to a user with the goal of improving focus, productivity, creativity, innovation, overall wellbeing, memory, healing, etc., while also reducing stress, anxiety, etc. The apparatus includes a support frame that defines a recess. An auditory signal generator is positioned to deliver an auditory signal to the recess. A somatosensory signal module is positioned to deliver a vibrotactile signal to the recess. The somatosensory signal module includes one or more vibrotactile signal generators, including one or more handheld vibrotactile signal generators and one or more peripheral vibrotactile signal generators. In some embodiments, the one or more peripheral vibrotactile signal generators are positioned to transmit the vibrotactile signal to acupressure points on the human body. An olfactive signal module, including a fragrance source, is positioned to deliver a fragrance to the recess. A visual signal module is positioned to deliver light to the recess.

The apparatus includes a communication module for controlling the signals generated by the olfactive signal module, the auditory signal generator, the vibrotactile signal generator, and/or the visual signal module, the communication module in communication with the olfactive signal module, the auditory signal generator, the vibrotactile signal generator, and/or the visual signal module.

One or more of these signals are delivered to the user by the multisensory environment apparatus during a "session," i.e., a set time period over which a protocol for using the apparatus is performed for and/or on the user. The delivery of the auditory and vibrotactile signals to the user work to meet the user's vital functions where they are, entrain them, and guide them to a more relaxed state, helping to reduce stress and anxiety, induce a meditative state and promote overall wellbeing. One or more sessions are thus performed over time, e.g. daily, monthly, etc., as part of an overall strategy to reduce stress and anxiety and promote overall wellbeing.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DESCRIPTION

Figure 1A:
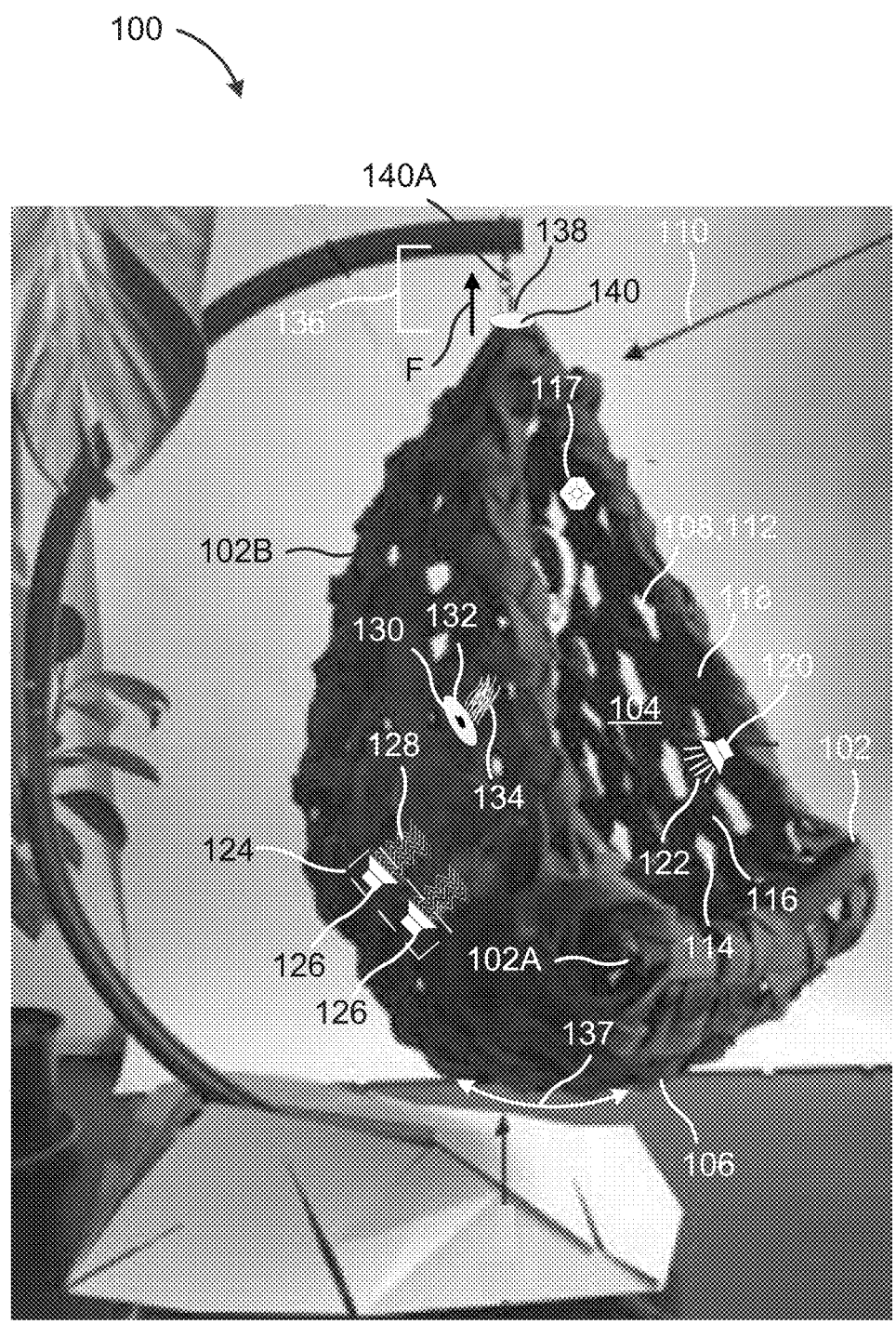
FIG. 1A is a schematic diagram of a multisensory environment apparatus for providing stress reduction to a user according to some embodiments of the present disclosure.
Figure 1B:
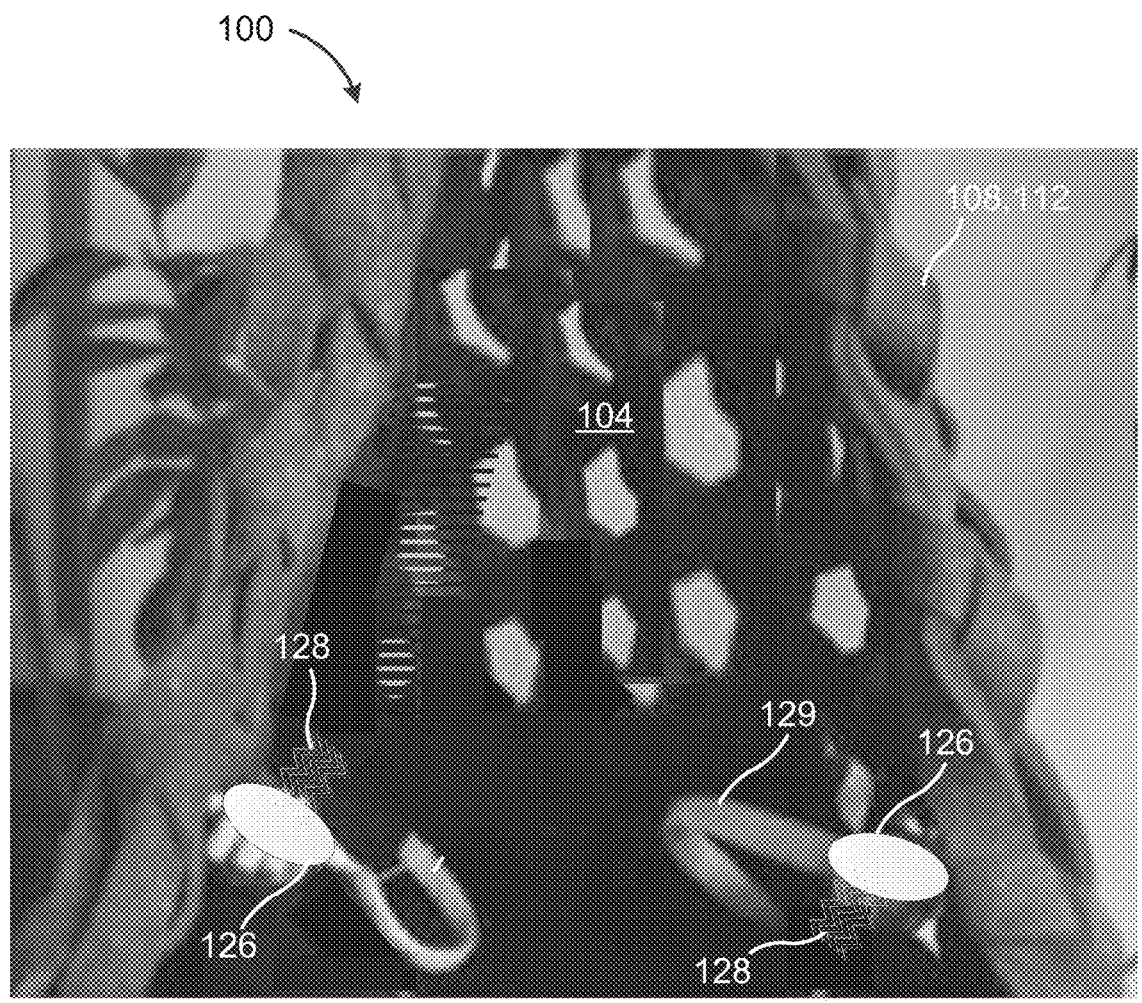
FIG. 1B is a schematic diagram of a multisensory environment apparatus for providing stress reduction to a user according to some embodiments of the present disclosure.

In some embodiments, the present disclosure is directed to a multisensory environment apparatus 100 for providing stress reduction to a user. Referring to FIGS. 1A-1B, in some embodiments, multisensory environment apparatus 100 includes a support frame 102 and a recess 104. In some embodiments, support frame 102 at least partially defines a recess 104. While the present disclosure shows and describes exemplary embodiments of the multisensory environment apparatus 100 as generally a chair, hammock, or bed, the apparatus is not limited in this regard. By way of example, support frame 102 can be the support structure for an exterior space, interior space of a building, automobile, passenger compartment of an automobile, boat, passenger compartment of a boat, airplane, passenger compartment of an airplane, other articles of furniture, e.g., cribs, articles of clothing, e.g., helmets, hooded sweatshirts, etc., or combinations thereof. In some embodiments, support frame 102 has a base portion 102A. In some embodiments, support frame 102 has a backing portion 102B. In some embodiments, backing portion 102B includes one or more first support features 102B' to stabilize the user in multisensory environment apparatus 100 and/or provide support for the modules and generators described below. In some embodiments, base portion 102A includes one or more second support features 102A' to secure the user in multisensory environment apparatus 100 and/or provide support for the modules and generators described below. Recess 104 is sized, configured, and positioned to accept the user into the multisensory environment created by multisensory environment apparatus 100, as will be discussed in greater detail below. In some embodiments, recess 104 is sized to accept an entire human body, e.g., an entire baby, an entire grown adult, etc. In some embodiments, recess 104 is sized to accept only a portion of the human body, e.g., only the head, only above the waist, etc. In some embodiments, the temperature within recess 104 is controlled, e.g., via heating and cooling elements (not pictured). In some embodiments, a seating mechanism 106 is positioned at least partially within recess 104. In some embodiments, seating mechanism 106 is attached to and/or supported by support frame 102. Seating mechanism 106 can be any suitable structure that enables a user to sit upon it and be positioned at least partially in recess 104, e.g., a chair, a bed, etc. In some embodiments, the user is a single user. In some embodiments, the user is two or more users, e.g., simultaneously. As will be discussed in greater detail below, multisensory environment apparatus 100 can be operated in one of at least two phases: a treatment phase and an energizing phase. In many embodiments, a session by the user with multisensory environment apparatus 100 includes a treatment phase followed by an energizing phase, although the present disclosure is not limited in this regard, and can include additional phases without departing from the present disclosure. The treatment phase is configured and designed to provide beneficial neurobiological, physiological and emotional changes reduce stress and/or anxiety, improve focus, productivity, creativity, innovation, overall wellbeing, memory, healing, etc. or combinations thereof. In some embodiments, the treatment phase is designed to provide beneficial neurobiological, physiological and emotional changes from a predetermined base state. As used herein, the term "predetermined base state" refers to the neurobiological, physiological, and/or emotional state of the user at the beginning of a session. In some embodiments, the predetermined base state is user-specific, e.g., the result of one or more sensor readings about the user. In some embodiments, the predetermined base state is environment-specific, e.g., the result of one or more sensor readings about multisensory environment apparatus 100. In some embodiments, the predetermined base state reflects a combination of user-specific and environment-specific data. In some embodiments, the predetermined base state is generic, i.e., a representation of an average "user" desiring a certain treatment or neurobiological, physiological and emotional change. The energizing phase is configured and designed to energize and bring the user toward and into a present, awake, and/or focused state, so that when the session is completed, the user is more prepared to perform. Each of the treatment phase and energizing phase are of variable length depending on the user and the desired session outcomes. For example, in some embodiments, the treatment phase is lengthened to account for higher levels of stress/anxiety in the user.

In some embodiments, multisensory environment apparatus 100 includes a visual signal module 108 positioned to deliver to recess 104 a visual signal 110, e.g., direct or diffuse ambient light. In some embodiments, visual signal 110 is natural light, electronic light, biological light, or combinations thereof, such as from an external lamp, the sun, and the like, or combinations thereof. While the present disclosure describes exemplary embodiments of multisensory environment apparatus 100 where visual signal 110 is direct or diffuse ambient light, the present disclosure is not limited in this regard. In some embodiments, visual signal 110 has a predetermined visual signal profile where the composition and intensity of the signal varies over time. In some embodiments, the visual signal profile has at least a first profile at a first instance, a second profile at a second instance, and a third profile at a final instance. In some embodiments, the visual signal profile oscillates between the first profile and the second profile. In some embodiments, the first visual signal profile is a baseline visual profile. In some embodiments, the first visual signal profile includes visual compositions and intensities designed to match a user's predetermined base state, including vital functions such as heart rate, breathing rate, etc., at the beginning of a session. In some embodiments, the second visual signal profile has decreased visual compositions and intensities, or combinations thereof relative to the first visual signal profile. The flow from the first visual signal profile to and through the second visual signal profile (treatment phase) occurs step-wise, continuously, or both, and is designed to entrain the user's vital functions and guide those vital functions from an elevated state to a reduced state. In some embodiments, the third visual signal profile has an increased visual composition and intensity or combinations thereof relative to the second visual signal profile. The flow from the second visual signal profile to and through the third visual signal profile (energizing phase) occurs step-wise, continuously, or both, and is designed to energize the user in preparation for the end of a session with multisensory apparatus 100.

In some embodiments, visual signal module 108 includes an enclosure portion 112. In some embodiments, enclosure portion 112 at least partially defines and enclosing recess 104. In some embodiments, enclosure portion 112 is semi-translucent. In some embodiments, the semi-translucent enclosure portion 112 includes a plurality of first regions 114 and a plurality of second regions 116, and the first regions are more light-transmissive than the second regions. In some embodiments, first regions 114 is composed of felt, wool fabric, cotton fabric, synthetic fabric, cellulose, linen, or combinations thereof. In some embodiments, visual signal module 108 is attached to and/or supports seating mechanism 106. In some embodiments, second region 116 are completely light-transmissive, e.g., are gaps in semi-translucent enclosure portion 112. In some embodiments, enclosure portion 112 is opaque. In some embodiments, enclosure portion 112 has variable translucence.

In some embodiments, enclosure portion 112 is configured to stabilize the user in multisensory environment apparatus 100 and/or provide support for the modules and generators described below. In some embodiments, the enclosure portion 112 is configured to operate as seating mechanism 106, e.g., semi-translucent enclosure portion 112 includes a base upon which a user can sit, positioning the user at least partially in recess 104. In some embodiments, semi-translucent enclosure portion 112 does not fully enclose recess 104, as will be discussed in greater detail below.

In some embodiments, visual signal module 108 includes one or more light sources 117. In some embodiments, light sources 117 are configured to oscillate between an on-state and an off-state. In some embodiments, the oscillation is gradual to give the impression that light source 117 is "breathing." In some embodiments, light sources 117 are configured to oscillate between at or near the same rate as the user's breathing rate. In some embodiments, light sources 117 oscillate at a first frequency at a first instance, a second frequency at a second instance, and a third frequency at a final instance. In some embodiments, light sources 117 alternate between any combination of the first frequency, the second frequency, and the third frequency during a session. In some embodiments, the oscillation starts at the first frequency and gradually decreases (step-wise, continuously, or both) to the second frequency. In some embodiments, the oscillation then increases to the third frequency.

In some embodiments, the amount of light and/or composition of light being delivered to recess 104, e.g., transmitted through enclosure portion 112, can be adjusted over the course of a session. By way of example, in some embodiments, a session begins by delivering only ambient light to recess 104. As the session progresses, additional light can be delivered, e.g., from light sources 117. Also, as the session progresses, the overall amount of light delivered to recess 104 can be reduced, e.g., all ambient light is eliminated, but some light from light sources 117 is added. In some embodiments, the overall amount of light is reduced to zero for some portion of the session. As a session draws to a close, the overall amount of light increases again. In some embodiments, the overall amount of light continues to increase even after a session has concluded.

In some embodiments, visual signal module 108 includes an opening 118 allowing communication between recess 104 and the environment surrounding multisensory environment apparatus 100. In some embodiments, opening 118 is maintained in an open conformation by support frame 102. Opening 118 is configured to enable a user to enter recess 104 from the surrounding environment.

In some embodiments, multisensory environment apparatus 100 includes an auditory signal generator 120. In some embodiments, auditory signal generator 120 is one or more sets of headphones. In some embodiments, auditory signal generator 120 is one or more speakers. Auditory signal generator 120 is positioned to deliver an auditory signal 122 to recess 104. Auditory signal 122 is generally composed of a plurality of tones, e.g., a song, soundscape, etc., emitted for hearing by the user at tempos and intensities designed to elicit a calming and/or stress-reducing physiological response from the user. In some embodiments, auditory signal 122 includes the user's own heartbeat, e.g., a previously recorded heartbeat, as currently beating heartbeat, etc. In some embodiments, auditory signal 122 includes pink noise. In some embodiments, auditory signal 122 includes melodic tones. In some embodiments, auditory signal 122 includes binaural beats. In some embodiments, auditory signal 122 has a predetermined auditory signal profile where the average frequency, tempo and/or the intensity of the signal varies over time. In some embodiments, the auditory signal profile has at least a first profile at a first instance, a second profile at a second instance, and a third profile at a final instance. In some embodiments, the first auditory signal profile is a baseline auditory profile. In some embodiments, the first auditory signal profile includes auditory frequencies, tempo, and intensity designed to match a user's predetermined base state, including vital functions such as heart rate, breathing rate, etc., at the beginning of a session. In some embodiments, the second auditory signal profile has decreased average frequency, decreased tempo, decreased intensity, or combinations thereof relative to the first auditory signal profile. The flow from the first auditory signal profile to and through the second auditory signal profile (treatment phase) occurs step-wise, continuously, or both, and is designed to entrain the user's vital functions and guide those vital functions from an elevated state to a reduced state. In some embodiments, the third auditory signal profile has an increased average frequency, increased tempo, increased intensity, or combinations thereof relative to the second auditory signal profile. The flow from the second auditory signal profile to and through the third auditory signal profile (energizing phase) occurs step-wise, continuously, or both, and is designed to energize the user in preparation for the end of a session with multisensory apparatus 100. In some embodiments, the auditory signal profile oscillates between the first profile and the second profile. In some embodiments, the auditory signal profile oscillates between the second profile and the third profile. In some embodiments, the third profile occurs before the second profile.

As discussed above, in some embodiments, auditory signal 122 includes binaural beats, e.g., the auditory signal 122 is split into first and second signals or channels having different frequencies. In some embodiments, the frequency difference between the two channels is maintained at about 3 Hz to about 12 Hz. In some embodiments, the frequency difference between the two channels is maintained at about 3 Hz to about 8 Hz. In some embodiments, the frequency difference between the two channels is maintained at about 8 Hz to about 12 Hz. The first auditory signal and the second auditory signal are delivered via different sources, e.g., left and right speakers in a set of headphones. Thus, in some embodiments, auditory signals 122 having different frequencies are delivered simultaneously, yet exclusively to different ears of the user. When signals having different frequencies are delivered to each ear, theta waves or alpha waves are created in the brain respectively. The theta waves have a soothing and calming physiological effect on the user. Should a different brainwave entrainment be required for the user's treatment, the settings can be adjusted accordingly.

In some embodiments, multisensory environment apparatus 100 includes a somatosensory signal module 124. Somatosensory signal module 124 includes one or more vibrotactile signal generators 126, positioned to deliver a vibrotactile signal 128. Vibrotactile signal 128 is delivered either locally or globally to recess 104. In some embodiments, vibrotactile signal 128 is continuous, i.e., at least one vibrotactile signal generator 126 is always vibrating while multisensory environment apparatus 100 is in use. In some embodiments, vibrotactile signal 128 is discontinuous. In some embodiments, vibrotactile signal generators 126 are handheld, peripheral, or combinations thereof. In some embodiments, vibrotactile signal generators 126 are integrated into support frame 102, seating mechanism 106, visual signal module 108, or combinations thereof. In some embodiments, vibrotactile signal generators 126 are aligned with acupressure points on the human body, e.g., the neck, shoulders, back, spine, buttocks, legs, or combinations thereof. In some embodiments, multisensory environment apparatus 100 includes at least 8 peripheral vibrotactile signal generators 126. In some embodiments, vibrotactile signal generators 126 are positioned for delivery of a signal that can be interpreted by the user's brain as affective touch on the user. In some embodiments, vibrotactile signal generators 126 are positioned relative to other components, such that vibrotactile signal 128 causes the other components to deliver a signal that can be interpreted by the user's brain as affective touch on the user.

Referring now to FIG. 1B, in some embodiments, multisensory environment apparatus 100 includes at least 2 handheld vibrotactile signal generators 126. Handheld vibrotactile signal generators 126 are shaped to be held comfortably in hand, e.g., generally spherical, egg-shaped, etc. In some embodiments, handheld vibrotactile signal generators 126 are free to be moved about recess 104 so that they can be held by the user in a variety of positions and orientations, both in relation to other vibrotactile signal generators 126 and in relation to the user. This freedom enables the user to position their hands where they are most comfortable, and also allows a user to place handheld vibrotactile signal generators 126 on other parts of their body, e.g., forehead, chest, stomach, etc.

Figure 2:
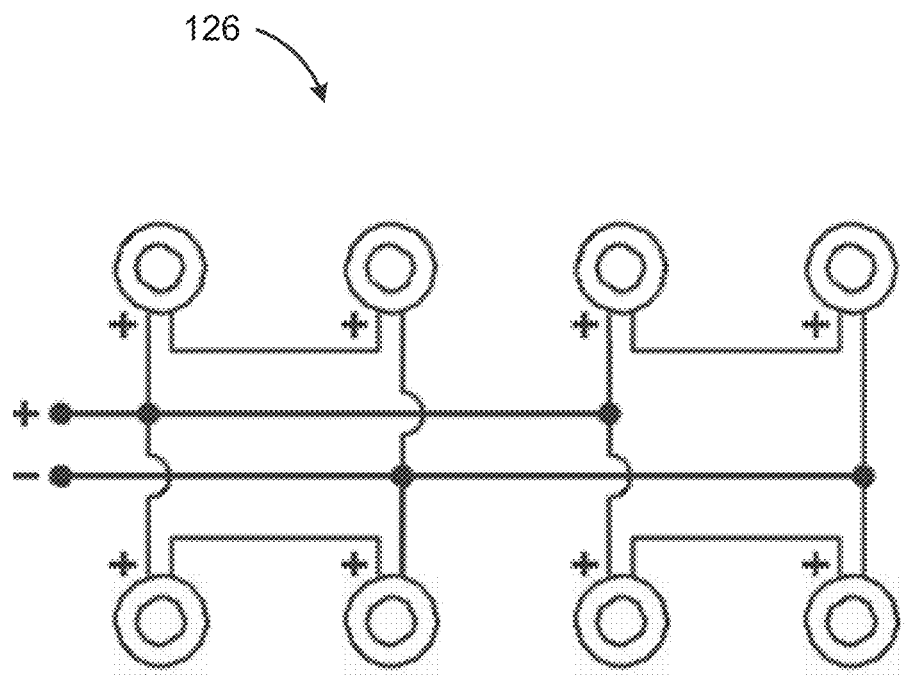
FIG. 2 is a wiring diagram of vibrotactile signal generators according to some embodiments of the present disclosure.

In some embodiments, vibrotactile signal generators 126 are wired in parallel. In some embodiments, vibrotactile signal generators 126 are wired in series. Referring now to FIG. 2, in some embodiments, a plurality of vibrotactile signal generators are wired in a series-parallel configuration. In some embodiments, vibrotactile signal generators 126 are wired so as to emit vibrotactile signal 128 substantially simultaneously. In some embodiments, vibrotactile signal generators 126 are wired so as to emit vibrotactile signal 128 in an ordered sequence. In some embodiments, vibrotactile signal generators 126 are wired so as to emit vibrotactile signal 128 in a random sequence. In some embodiments, vibrotactile signal generators 126 are wired so as to emit vibrotactile signal 128 randomly.

Referring again to FIG. 1A, in some embodiments, vibrotactile signal 128 includes a predetermined vibrotactile signal profile where the frequency, tempo, and/or the intensity of the signal varies over time. In some embodiments, the vibrotactile signal profile has at least a first profile at a first instance, a second profile at a second instance, and a third profile at a final instance. In some embodiments, the first vibrotactile signal profile is a baseline vibrotactile profile. In some embodiments, the first vibrotactile signal profile includes vibrotactile frequencies, tempo, and intensity designed to match a user's predetermined base state, including vital functions such as heart rate, breathing rate, etc., at the beginning of a session. In some embodiments, the second vibrotactile signal profile has decreased average frequency, decreased tempo, decreased intensity, or combinations thereof relative to the first vibrotactile signal profile. Similarly to the auditory signal profile, the flow from the first vibrotactile signal profile to and through the second vibrotactile signal profile (treatment phased) occurs step-wise, continuously, or both, and is designed to entrain the user's vital functions and guide those vital functions from an elevated state to a reduced state. In some embodiments, the third vibrotactile signal profile has an increased average frequency, increased tempo, increased intensity, or combinations thereof relative to the second vibrotactile signal profile. Again, similarly to the auditory profile, the flow from the second vibrotactile signal profile to and through the third vibrotactile signal profile (energizing phase) occurs step-wise, continuously, or both, and is designed to energize the user in preparation for the end of a session with multisensory apparatus 100. In some embodiments, one or more of the phases can be omitted. In some embodiments, vibrotactile signal 128 and auditory signal 122 are synchronous, i.e., they vary similarly or identically over time. In some embodiments, the vibrotactile signal profile oscillates between the second profile and the third profile. In some embodiments, the third profile occurs before the second profile.

In some embodiments, vibrotactile signal 128 is identical to auditory signal 122, but is instead delivered to recess 104 merely as vibration rather than sound. In some embodiments, vibrotactile signal generators 126 are exciter speakers, an oscillating mass, etc., or combinations thereof. Without wishing to be bound by theory, delivery of vibrotactile signal 128 in this way activates sensory processing centers and pleasantness processing centers in the brain, initiating releases of compounds such as oxytocin, which, among other things, suppress the activity of the stress-induced HPA axis and reduce the release of adrenocorticotropic hormone.

In some embodiments, multisensory environment apparatus 100 includes an olfactive signal module 130. Olfactive signal module 130 includes an odorant source 132 positioned to deliver an olfactive signal 134 to recess 104. In some embodiments, olfactive signal 134 is includes one or more odorants. In some embodiments, odorant source 132 is one or more odorants embedded in multisensory environment apparatus 100, e.g., in support frame 102, visual signal module 108, or combinations thereof. In some embodiments, odorant source 132 is a diffuser configured to hold and emit one or more odorants, thus producing an olfactive profile where emitted. In some embodiments, odorant source 132 is controlled manually. Olfactive signal 134 includes a predetermined olfactive profile where the composition of aroma compounds and/or intensity, e.g., concentration, of the olfactive signal and/or its independent compounds vary over time. In some embodiments, olfactive signal 134 has at least a first olfactive profile at a first instance and a second olfactive profile at a second instance. The olfactive profiles help induce neurobiological, physiological and emotional responses in the user that achieve specific brain states. Without wishing to be bound by theory, the first olfactive profile is designed to build trust by activating the V1N1 receptor and limbic regions, to promote healing and to induce the physiological state of relaxation, amongst other things. This first olfactive profile is thus useful prior to, at the beginning of, and during a session (treatment phase). The second olfactive profile is designed to have an arousing, activating or energizing effect on the user (energizing phase). This second olfactive profile is thus useful near the end of the session and after the session is completed. In some embodiments, the second olfactive profile is delivered during and/or at the beginning of the energizing phase. In some embodiments, the first olfactive profile includes hedione, musk, lavender, sandalwood, sandalore, and the like, or combinations thereof. In some embodiments, the first olfactive profile varies in composition and/or intensity over time. In some embodiments, the second olfactive signal includes odorants falling under the citrus classification.

In some embodiments, multisensory environment apparatus 100 includes a vestibular signal module 136. Vestibular signal module 136 is positioned to deliver a vestibular signal 137 to recess 104. In some embodiments, vestibular signal 137 affects linear acceleration by introducing a sense of rocking, movement, or change of position. Vestibular signal 137 can be delivered in the form of physical movement of multisensory environment apparatus 100, e.g., suspension and/or rocking of the apparatus itself, or in the form of visual and/or audio cues that alter the user's sense of balance and orientation, e.g., via auditory signal generator 120, vibrotactile signal generator 126, visual signal module 108, virtual reality headset, and the like, or combinations thereof. In some embodiments, vestibular signal 137 has a predetermined vestibular signal profile where the composition and intensity of the signal varies over time. Each vestibular signal profile includes a different sense of rocking, movement, change of position, or combination thereof. The flow between the vestibular signal profiles occurs step-wise, continuously, or both, and is designed to soothe and calm the user. In some embodiments, the vestibular signal profile oscillates between the second profile and the third profile. In some embodiments, the third profile occurs before the second profile.

In some embodiments, vestibular signal module 136 includes one or more mounting points 138 in order to position multisensory environment apparatus 100 in a surrounding environment. Mounting points 138 are positioned such that multisensory environment apparatus 100 can become imbalanced and will settle into a state of equilibrium, e.g., when a user enters recess 104. In some embodiments, mounting points 138 are positioned to suspend multisensory environment apparatus 100 from above, e.g., from the ceiling or an overhead support. In some embodiments, multisensory environment apparatus 100 is suspended from a single mounting zone 140, i.e., via a single independent tension force F. Each mounting zone 140 includes one or more suspenders 140A. In some embodiments, the single mounting zone 140 includes two or more suspenders 140A.

In some embodiments, vestibular signal module 136 includes two or more mounting zones 140. In some embodiments, two or more mounting zones 140 are positioned in a middle region of multisensory environment apparatus 100. In some embodiments, two or more mounting zones 140 are positioned in a lower region of multisensory environment apparatus 100. Without wishing to be bound by theory, the vestibular signal 137 introduces a perception of rocking, motion, change of position, change of spatial understanding or any combination there of in the user, which results in a synchronization of complex brainwave activity and increase in slow wave activity in the user.

Figure 1C:
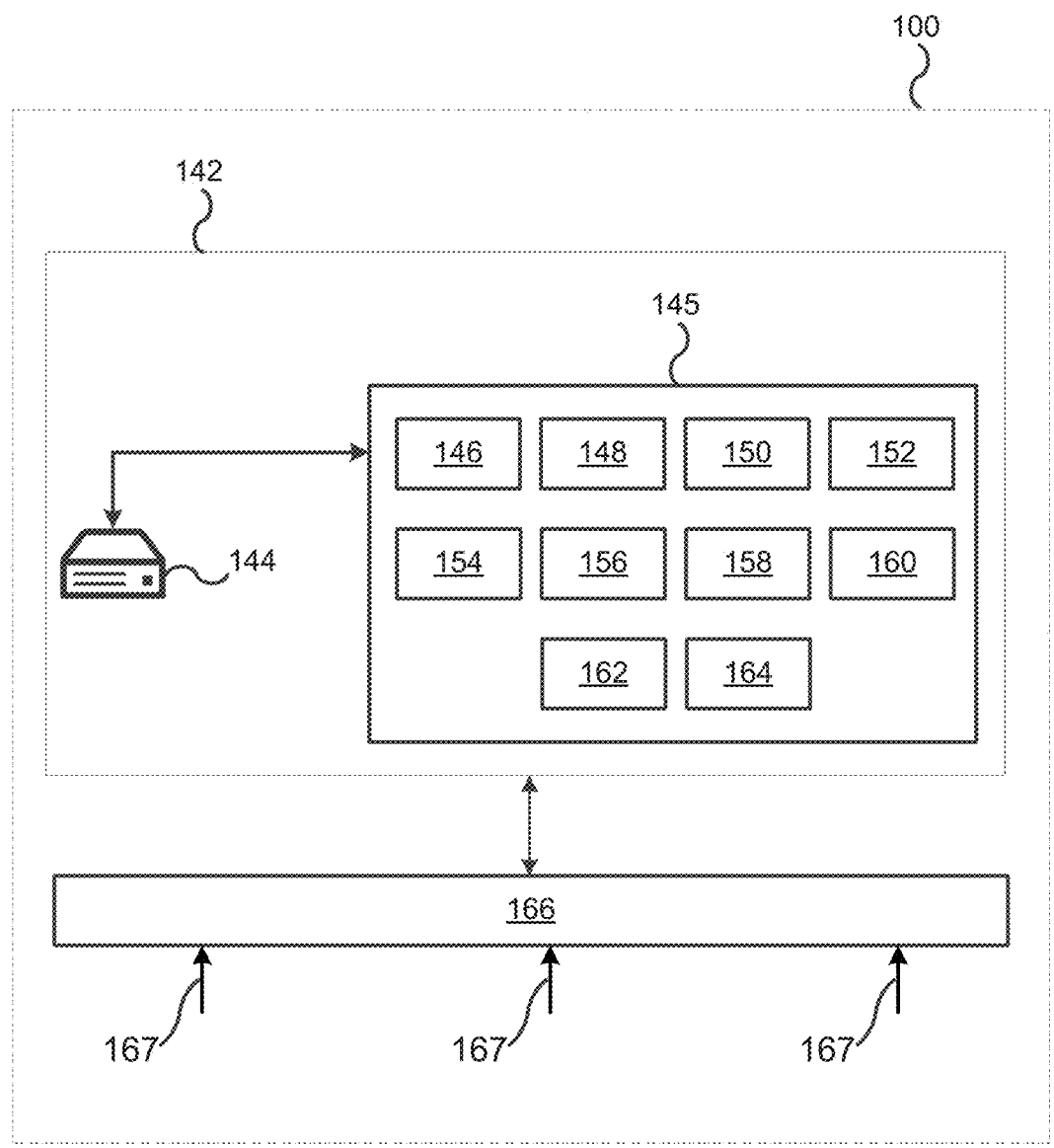
FIG. 1C is a schematic diagram of a communication module for controlling a multisensory environment apparatus according to some embodiments of the present disclosure.

Referring now to FIG. 1C, in some embodiments, multisensory environment apparatus 100 includes a communication module 142 for controlling the signals generated by olfactive signal module 130, auditory signal generator 120, vibrotactile signal generator 126, visual signal module 108, and/or vestibular signal module 136. Communication module 142 is in communication, e.g., wireless, wired, or combinations thereof, with olfactive signal module 130, auditory signal generator 120, vibrotactile signal generator 126, visual signal module 108, vestibular signal module 136, or combinations thereof.

Communication module 142 includes a non-transitory computer storage medium 144 encoded with one or more computer programs 145. In some embodiments, the one or more computer programs include a heart rate module 146 in communication with olfactive signal module 130, auditory signal generator 120, vibrotactile signal generator 126, visual signal module 108, and/or vestibular signal module 136. Heart rate module 146 is configured to monitor the heart rate of a user, asses a baseline heart rate, and establish olfactive signal 134, auditory signal 122, vibrotactile signal 128, visual signal 110, and/or vestibular signal 137 at a baseline profile based on an initial heat rate of the user. In some embodiments, heart rate module 146 is also configured to adjust the baseline profiles of olfactive signal 134, auditory signal 122, vibrotactile signal 128, visual signal 110, and/or vestibular signal 137 with changes in the user's heart rate. By way of example, in some embodiments, heart rate module 146 is configured to communicate with olfactive signal module 130, auditory signal generator 120, vibrotactile signal generator 126, visual signal module 108, vestibular signal module 136 to emit olfactive signal 134, auditory signal 122, vibrotactile signal 128, visual signal 110, and/or vestibular signal 137 consistent with the associated signal profiles discussed above in order to entrain and reduce the user's heart rate during a session and energize the user for after the session. In some embodiments, user heart rate data is collected over time to better tailor olfactive signal 134, auditory signal 122, vibrotactile signal 128, visual signal 110, and/or vestibular signal 137 to the user for subsequent sessions.

In some embodiments, the one or more computer programs 145 include a breath analysis module 148 in communication with olfactive signal module 130, auditory signal generator 120, vibrotactile signal generator 126, visual signal module 108, and/or vestibular signal module 136. Breath analysis module 148 is configured to monitor aspects of the user's breathing, such as breath rate, breath volume, exhalation force, breath composition, oxygen levels, etc., and establish olfactive signal 134, auditory signal 122, vibrotactile signal 128, visual signal 110, and/or vestibular signal 137 at a baseline profile based on an initial breath analysis of the user. Breath rate module 148 is also configured to adjust the baseline profiles of olfactive signal 134, auditory signal 122, vibrotactile signal 128, visual signal 110, and/or vestibular signal 137 with changes in the user's breathing. By way of example, breath rate module 148 is configured to communicate with olfactive signal module 130, auditory signal generator 120, vibrotactile signal generator 126, and/or visual signal module 108 to emit olfactive signal 134, auditory signal 122, vibrotactile signal 128, visual signal 110, and/or vestibular signal 137 consistent with the associated signal profiles discussed above in order to entrain and reduce the user's breath rate during a session and energize the user for after the session. In some embodiments, user breath analysis data is collected over time to better tailor olfactive signal 134, auditory signal 122, vibrotactile signal 128, visual signal 110, and/or vestibular signal 137 to the user for subsequent sessions.

In some embodiments, the one or more computer programs 145 include a user movement module 150 in communication with olfactive signal module 130, auditory signal generator 120, vibrotactile signal generator 126, visual signal module 108, and/or vestibular signal module 136. The user movement module 150 is configured to monitor muscle movement, e.g., amount or quality of movement, of a user, and establish olfactive signal 134, auditory signal 122, vibrotactile signal 128, visual signal 110, and/or vestibular signal 137 at a baseline profile based on the user's initial muscle movement. User movement module 150 is also configured to adjust the baseline profiles of olfactive signal 134, auditory signal 122, vibrotactile signal 128, visual signal 110, and/or vestibular signal 136 with changes in the user's muscle movement. By way of example, user movement module 150 is configured to communicate with olfactive signal module 130, auditory signal generator 120, vibrotactile signal generator 126, visual signal module 108, and/or vestibular signal module 136 to emit olfactive signal 134, auditory signal 122, vibrotactile signal 128, visual signal 110, and/or vestibular signal 137 consistent with the associated signal profiles discussed above in order to calm a user's muscle movement during a session and energize the user for after the session. In some embodiments, user muscle movement data is collected over time to better tailor olfactive signal 134, auditory signal 122, vibrotactile signal 128, visual signal 110, and/or vestibular signal 137 to the user for subsequent sessions.

In some embodiments, the one or more computer programs 145 include a blood pressure module 152 in communication with olfactive signal module 130, auditory signal generator 120, vibrotactile signal generator 126, visual signal module 108, and/or vestibular signal module 136. The blood pressure module 152 is configured to monitor the blood pressure of a user, and establish olfactive signal 134, auditory signal 122, vibrotactile signal 128, visual signal 110, and/or vestibular signal 137 at a baseline profile based on the user's initial blood pressure. Blood pressure module 142 is also configured to adjust the baseline profiles of olfactive signal 134, auditory signal 122, vibrotactile signal 128, and/or visual signal 110, and/or vestibular signal 137 with changes in the user's blood pressure. By way of example, in some embodiments, blood pressure module 152 is configured to communicate with olfactive signal module 130, auditory signal generator 120, vibrotactile signal generator 126, and/or visual signal module 108 to emit olfactive signal 134, auditory signal 122, vibrotactile signal 128, visual signal 110, and/or vestibular signal 137 consistent with the associated signal profiles discussed above in order to lower a user's blood pressure during a session and energize the user for after the session. In some embodiments, user blood pressure data is collected over time to better tailor olfactive signal 134, auditory signal 122, vibrotactile signal 128, visual signal 110, and/or vestibular signal 137 to the user for subsequent sessions.

In some embodiments, the one or more computer programs 145 include a skin conductivity module 154 in communication olfactive signal module 130, auditory signal generator 120, vibrotactile signal generator 126, visual signal module 108, and/or vestibular signal module 136. The skin conductivity module 154 is configured to monitor skin conductivity of a user, and establish olfactive signal 134, auditory signal 122, vibrotactile signal 128, visual signal 110, and/or vestibular signal 136 at a baseline profile based on the user's initial skin conductivity. Skin conductivity module 154 is also configured to adjust the baseline profiles of olfactive signal 134, auditory signal 122, vibrotactile signal 128, visual signal 110, and/or vestibular signal 137 with changes in the user's skin conductivity. By way of example, skin conductivity module 154 is configured to communicate with olfactive signal module 130, auditory signal generator 120, vibrotactile signal generator 126, and/or visual signal module 108 to emit olfactive signal 134, auditory signal 122, vibrotactile signal 128, visual signal 110, and/or vestibular signal 137 consistent with the associated signal profiles discussed above in order to relax the user during a session and energize the user for after the session. In some embodiments, user skin conductivity data is collected over time to better tailor olfactive signal 134, auditory signal 122, vibrotactile signal 128, visual signal 110, and/or vestibular signal 137 to the user for subsequent sessions.

In some embodiments, the one or more computer programs 145 include an electroencephalogram module 156 in communication with the olfactive signal module 130, auditory signal generator 120, vibrotactile signal generator 126, visual signal module 108, and/or vestibular signal module 136. The electroencephalogram module 156 is configured to monitor electrical activity and measure brain waves in the brain of a user, and establish olfactive signal 134, auditory signal 122, vibrotactile signal 128, visual signal 110, and/or vestibular signal 137 at a baseline profile based on the user's measured brain waves. Electroencephalogram module 156 is also configured to adjust the baseline profile with changes in the user's measured brain waves. By way of example, electroencephalogram module 156 is configured to communicate with olfactive signal module 130, auditory signal generator 120, vibrotactile signal generator 126, and/or visual signal module 108 to emit olfactive signal 134, auditory signal 122, vibrotactile signal 128, visual signal 110, and/or vestibular signal 137 consistent with the associated signal profiles discussed above in order to balance brain waves of the user during a session and energize the user for after the session. In some embodiments, user electroencephalography data is collected over time to better tailor olfactive signal 134, auditory signal 122, vibrotactile signal 128, visual signal 110, and/or vestibular signal 137 to the user for subsequent sessions.

In some embodiments, the one or more computer programs 145 includes a behavioral data module 158 in communication with the olfactive signal module 130, auditory signal generator 120, vibrotactile signal generator 126, visual signal module 108, and/or vestibular signal module 136. The behavioral data module 158 is configured to establish olfactive signal 134, auditory signal 122, vibrotactile signal 128, visual signal 110, and/or vestibular signal 137 at a baseline profile based on behavioral data of the user. In some embodiments, user behavioral data is updated over time to better tailor olfactive signal 134, auditory signal 122, vibrotactile signal 128, visual signal 110, and/or vestibular signal 137 to the user for subsequent sessions. In some embodiments, user behavioral data is provided via third-party sources, e.g., fitness applications, dietary tracking applications, other applications, smart watches, fitness trackers, other wearable apparatus, smart and other connected devices, e.g., smartphones, etc.

In some embodiments, the one or more computer programs 145 includes a facial recognition module 160 in communication with the olfactive signal module 130, auditory signal generator 120, vibrotactile signal generator 126, visual signal module 108, and/or vestibular signal module 136. In some embodiments, facial recognition module 160 is configured to verify the identity of a user for a session. In some embodiments, the facial recognition module 160 is configured to read the emotional state of the user. The facial recognition module 160 is configured to control olfactive signal 134, auditory signal 122, vibrotactile signal 128, visual signal 110, and/or vestibular signal 137 based the identity of the user. In some embodiments, facial recognition module 160 includes user personal preferences, e.g., for olfactive signal 134, auditory signal 122, vibrotactile signal 128, visual signal 110, and/or vestibular signal 137, and is configured to establish the user personal preferences upon verification of the user.

In some embodiments, the one or more computer programs 145 include a scent module 162 in communication with olfactive signal module 130. Scent module 162 is configured to control an olfactive profile, e.g., odorant concentration, in recess 104.

In some embodiments, the one or more computer programs 145 include a sound module 164 in communication with auditory signal generator 120 and vibrotactile signal generator 126. In some embodiments, sound module 164 is configured to send auditory signal 122 to auditory signal generator 120 and vibrotactile signal 128 to vibrotactile signal generator 126. In some embodiments, sound module 164 is configured to split auditory signal 122 between at least one first channel and at least one second channel, and then send at least one first channel to auditory signal generator 120 and the at least one second channel being sent to vibrotactile signal generator 126. In some embodiments, sound module 164 is configured to synchronize auditory signal 122 and vibrotactile signal 128.

In some embodiments, multisensory environment apparatus 100 includes additional sensors (not pictured) for measuring and/or identifying certain aspects of the user, apparatus components, surrounding environment, or combinations thereof. These sensors include, but are not limited to, skin conductivity sensors; spit test analysis, lab-on-a-chip sensors, e.g., saliva testing sensors; temperature sensors;

vocal analysis sensors; facial recognition sensors; movement sensors, e.g., muscle movement sensors, eye movement tracking sensors; blood pressure sensors; electroencephalographs; sensors configured to monitor the surrounding environment, or combinations thereof.

In some embodiments, one or more sensors such as those described above constitute a sensor module 166. These sensors are in communication with olfactive signal module 130, auditory signal generator 120, vibrotactile signal generator 126, visual signal module 108, vestibular signal module 136, communication module 142 (as shown in FIG. 1C), or combinations thereof. Sensor module 166 is configured to measure, monitor, and/or record signals 167 from these sensors. In some embodiments, one or more of these signals 167 describe a predetermined base state of the user and/or base state of multisensory environment apparatus 100. In some embodiments, the base profiles described above, e.g., baseline auditory profile, etc., are then configured to treat a predetermined base state of the user (or alter the base state of multisensory environment apparatus 100) to achieve the desired treatment outcome, e.g., improving focus, productivity, creativity, innovation, overall wellbeing, memory, healing, etc.; reducing stress, anxiety, etc.; or combinations thereof.

In some embodiments, one or more of these signals 167 identify the state of the user and/or state of multisensory environment apparatus 100 during a session. In some embodiments, changes over time for one or more of these signals 167 identify the progression of the user's state and/or multisensory environment apparatus 100's state throughout or during a session. These changes in signals 167 reflect changes in the user, multisensory environment apparatus 100, or the surrounding environment. Signal profiles, e.g., first/second auditory signal profile, etc., can be adjusted in response to the signals 167 in order to create a more beneficial treatment profile for the user. In some embodiments, the signal profiles described above, e.g., first/second auditory signal profile, etc., are emitted, altered, or stopped in response to how signals 167 change throughout a session.

Figure 3:
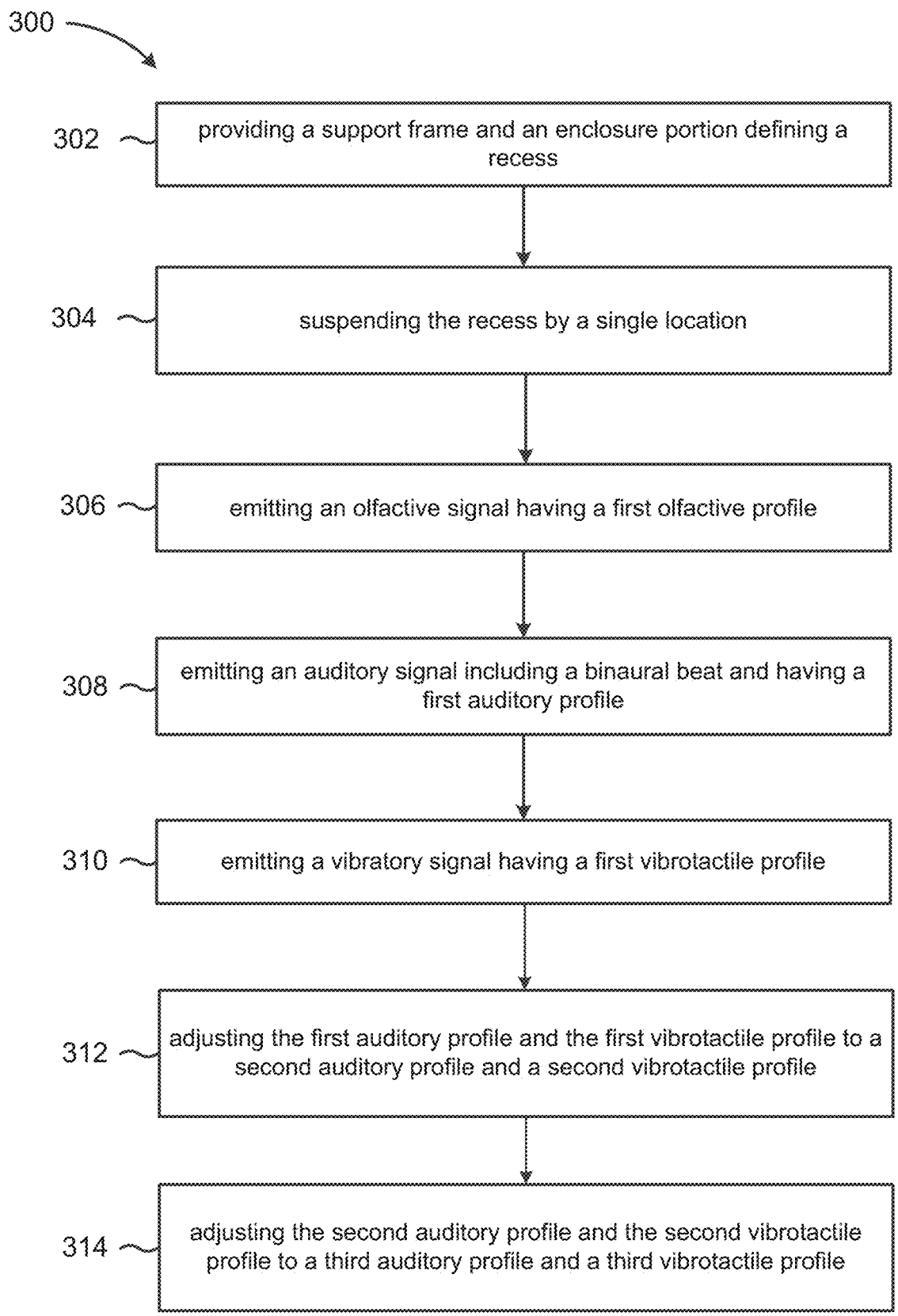
FIG. 3 is a chart of a method for reducing stress via a multisensory environment according to some embodiments of the disclosure subject matter.

Referring now to FIG. 3, the present disclosure is directed to a method 300 of providing a multisensory environment and producing physiological effects in a user within the multisensory environment. In some embodiments, method 300 constitutes a protocol to be followed one or more times, e.g., in one or more "sessions," at certain intervals over a length of time in an overall effort to reduce baseline user stress levels over time and/or improve baseline user vital physiological, emotional and neurobiological baseline functions. The overall duration of a session is user dependent, and can be made longer or shorter based on scheduling constraints, stress level, level of stress reduction, other desired effects, or combinations thereof. At 302, a support frame and an enclosure portion defining a recess are provided. At 304, the recess is suspended by a single location, e.g. by the support frame, enclosure portion, or combinations thereof. At 306, an olfactive signal having a first olfactive profile is emitted, e.g., delivered to the recess. At 308, an auditory signal including binaural beats is emitted, e.g., delivered to the recess, the auditory signal having a first auditory profile. At 310, a vibrotactile signal is emitted, e.g., delivered to the recess, the vibrotactile signal having a first vibrotactile profile. At 312, the first auditory profile and the first vibrotactile profile are adjusted to a second auditory profile and a second vibrotactile profile. As discussed above, in some embodiments, an olfactive signal having a second olfactive profile is provided to the recess subsequent to the second auditory profile and the second vibrotactile profile.

At 314, the second auditory profile and the second vibrotactile profile are adjusted to a third auditory profile and a third vibrotactile profile.

The multisensory environment apparatus of the present disclosure and the multisensory environment it creates produce measurable physiological benefits to the user. Each signal, alone and in combination with the other signals, are specifically design to guide the user's brain state to more relaxed and/or balanced levels. In some embodiments, the first impression that multisensory environment apparatus 100 makes on the user is through visual signal module 108. Visual signal module 108 is composed of materials that appear warm, soft, and comfortable, so that the user is not intimidated by multisensory environment apparatus 100. Rather, the user feels invited and comforted by visual signal module 108, and is thus more open to guidance by and interaction with the apparatus. Once positioned within recess 104, the user is not isolated from the surrounding environment. For example, opening 118 ensures that the user is never completely enclosed by semi-translucent enclosure portion 112. Additionally, second regions 116 allow the user to view the surrounding environment, so the user is less inclined to feel trapped or restrained, which could trigger the beginnings of or full fight-or-flight responses and increase stress. Again, visual signal module 108 is composed of materials that appear warm, soft, and comfortable, so a user in recess 104 is in contact with and or surrounded by these materials, contributing to a sense that the user is being comforted and cossetted, but on their own terms. Thus visual signal module 108 is highly advantageous in initiating a reduction in stress levels for the user and for maintaining an environment for reduction of stress during a session.

Olfactive signal module 130 also contributes to the positive first impression that multisensory environment apparatus 100 makes on the user. As discussed above, the first olfactive profile is designed to have a welcoming, trust promoting and calming effect on the user, so that upon approaching multisensory environment apparatus 100 to start a session, the user is more inclined to feel invited and comforted than concerned and skeptical. Towards the end of a session, the second olfactive profile is effective to energize the user so that the user feels a sense of momentum to perform post-session activities. Olfactive signal module 130 is also specifically designed to deliver these signals to a user while positioned in recess 104. Therefore, like the visual signal module 108 discussed above, the olfactive signal module 130 is highly advantageous in initiating and maintaining an environment for the reduction of stress, while also preparing the user to resume activity afterwards. Multisensory environment apparatus 100 is thus more easily integrated into a user's daily routine or schedule.

Once settled into recess 104, the auditory signal generator 120 and vibrotactile signal generator 126 are positioned specifically to deliver stress reducing signals to the user. As discussed above, auditory signal 122 includes a binaural beat and pink noise, the delivery of which alters the brain state of the user, producing an increase in meditative and relaxing alpha and theta waves. Auditory signal 122 is mirrored by vibrotactile signal 128, but delivered only as vibrations (not audio) and delivered to acupressure points (and hands and/or wherever the user desires to place them) on the user rather than into the user's ears. In some embodiments, the delivery of olfactive signal 134 also mirrors the delivery of auditory signal 122 and vibrotactile signal 128. The combined, and in some cases synchronous, delivery of these signals further contributes a feeling of active relaxation in the user. The auditory and vibrotactile signal profiles also work to meet the user's vital functions where they are, entrain them, and guide them to a more relaxed state, helping to reduce stress. As with the olfactory signal, towards the end of a session, the auditory and vibrotactile signals work together to energize the user so that the user feels a sense of momentum to perform post-session activities, such as by increasing in tempo and/or intensity.

Finally, once the user has settled into recess 104, multisensory environment apparatus 100 works on the balance system through user-perceived movements, such as rocking, which have a soothing effect themselves.

These advantages combine to have an immediate physiological effect on the user, with resulting benefits includes improved energy, focus, learning ability, performance, and mood. Additionally, one or more sessions can be performed over time, e.g. daily, weekly, monthly, etc. Thus use of multisensory environment apparatus 100 is advantageous as a regimen to reduce stress and maintain lower stress levels in a user. Repeated user of multisensory environment apparatus 100 also trains the user's body to return to lowers stress levels on their own, helping to break the cycle of stress.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:

1. A multisensory environment apparatus comprising:
a support frame;
an enclosure portion;
a recess defined by the support frame, the enclosure portion, or combinations thereof;
an auditory signal generator positioned to deliver an auditory signal to the recess;
a vibrotactile signal generator positioned to deliver a vibrotactile signal to the recess;
an olfactive signal module comprising an odorant source positioned to deliver an odorant to the recess;
a vestibular signal module including a single mounting zone for suspending the apparatus, the mounting zone having an independent tension force applied thereto for suspending the apparatus; and
a communication module for controlling the signals generated by the olfactive signal module, the auditory signal generator, the vibrotactile signal generator, the visual signal module, or combinations thereof, the communication module in communication with the olfactive signal module, the auditory signal generator, the vibrotactile signal generator, the visual signal module, or combinations thereof.

2. The apparatus according to claim 1, further comprising a seating mechanism positioned within the recess.

3. The apparatus according to claim 1, further comprising a visual signal module positioned to deliver light to the recess, wherein the visual signal module includes the enclosure portion.

4. The apparatus according to claim 3, wherein the enclosure portion is semi-transparent and includes a plurality of first regions and a plurality of second regions, wherein the first regions are more light-transmissive than the second regions.

5. The apparatus according to claim 3, further comprising an opening defined by the visual signal module, maintained by the support frame, and in communication with an environment surrounding the apparatus, wherein the opening is configured to enable a user to enter the recess from the surrounding environment.

6. The apparatus according to claim 1, wherein the olfactive signal module includes a diffuser integrated into the visual signal module, the support frame, or combinations thereof.

7. The apparatus according to claim 1, wherein the odorant includes a first olfactive profile at a first instance and a second olfactive profile at a second instance.

8. The apparatus according to claim 1, wherein
the auditory signal has a predetermined auditory profile, wherein the predetermined auditory signal profile has a first auditory profile at a first instance, a second auditory profile at a second instance, and a third auditory profile at a final instance; and
the auditory signal includes pink noise.

9. The apparatus according to claim 1, wherein the auditory signal includes binaural beats, wherein a first frequency delivered to a first ear of the user and a second frequency delivered to a second ear of the user, the difference between the first frequency and the second frequency being maintained at about 3 Hz to about 12 Hz.

10. The apparatus according to claim 1, wherein one or more vibrotactile signal generators are handheld, integrated into a visual signal module, integrated into the support frame, aligned with acupressure points on the human body, or combinations thereof.

11. The apparatus according to claim 1, wherein one or more vibrotactile signal generators are positioned for delivery of a signal that can be interpreted by the user's brain as affective touch on the user.

12. The apparatus according to claim 1, wherein the auditory signal and the vibrotactile signal are synchronous.

13. The apparatus according to claim 1, wherein the communication module includes a non-transitory computer storage medium encoded with one or more computer programs, the one or more computer programs including
a heart rate module in communication with the olfactive signal module, the auditory signal generator, the vibrotactile signal generator, a visual signal module, or combinations thereof, wherein the heart rate module is configured to monitor the heart rate of a user, establish an olfactive, auditory, vibrotactile, or visual signal at a baseline profile based on an initial heat rate of the user, and adjust the baseline profile with changes in the user's heart rate;
a breath analysis module in communication with the olfactive signal module, the auditory signal generator, the vibrotactile signal generator, the visual signal module, or combinations thereof, wherein the breath analysis module is configured to monitor the breath of a user, establish an olfactive, auditory, vibrotactile, or visual signal at a baseline profile based on an initial breath analysis for the user, and adjust the baseline profile with changes in the user's breathing;
a user movement module in communication with the olfactive signal module, the auditory signal generator, the vibrotactile signal generator, the visual signal module, or combinations thereof, wherein the user movement module is configured to monitor muscle movement of a user, establish an olfactive, auditory, vibrotactile, or visual signal at a baseline profile based on the user's initial muscle movement, and adjust the baseline profile with changes in the user's muscle movement;

a blood pressure module in communication with the olfactive signal module, the auditory signal generator, the vibrotactile signal generator, the visual signal module, or combinations thereof, wherein the blood pressure module is configured to monitor the blood pressure of a user, establish an olfactive, auditory, vibrotactile, or visual signal at a baseline profile based on the user's initial blood pressure, and adjust the baseline profile with changes in the user's blood pressure;

a skin conductivity module in communication with the olfactive signal module, the auditory signal generator, the vibrotactile signal generator, the visual signal module, or combinations thereof, wherein the skin conductivity module is configured to monitor skin conductivity of a user, establish an olfactive, auditory, vibrotactile, or visual signal at a baseline profile based on the user's initial skin conductivity, and adjust the baseline profile with changes in the user's skin conductivity;

an electroencephalogram module in communication with the olfactive signal module, the auditory signal generator, the vibrotactile signal generator, the visual signal module, or combinations thereof, wherein the electroencephalogram module is configured to monitor electrical activity and measure brain waves in the brain of a user, establish an olfactive, auditory, vibrotactile, or visual signal at a baseline profile based on the user's measured brain waves, and adjust the baseline profile with changes in the user's measured brain waves;

a behavioral data module in communication with the olfactive signal module, the auditory signal generator, the vibrotactile signal generator, the visual signal module, or combinations thereof, wherein the behavioral data module is configured to establish an olfactive, auditory, vibrotactile, or visual signal at a baseline profile based on behavioral data of the user;

a facial recognition module in communication with the olfactive signal module, the auditory signal generator, the vibrotactile signal generator, the visual signal module, or combinations thereof, wherein the facial recognition module is configured to control an olfactive, auditory, vibrotactile, or visual signal based the identity of the user;

a scent module in communication with the olfactive signal module, the scent module configured to control an odorant concentration in the recess; and a sound module in communication with the auditory signal generator and the vibrotactile signal generator, the sound module configured to split the auditory signal between at least one first channel and at least one second channel, the at least one first channel being sent to the auditory signal generator and the at least one second channel being sent via the vibrotactile signal generator.

14. A multisensory environment apparatus comprising:
a support frame;
an enclosure portion;
a recess defined by the support frame, the enclosure portion, or combinations thereof;
an olfactive signal module comprising an odorant source positioned to deliver a fragrance to the recess;
a visual signal module positioned to deliver light to the recess;
an auditory signal generator positioned to deliver an auditory signal to the recess, the auditory signal including a binaural beat; and
a somatosensory signal module, wherein the somatosensory signal module includes:
one or more handheld vibrotactile signal generators;
one or more peripheral vibrotactile signal generators;
a vibrotactile signal generated from the handheld and peripheral vibrotactile signal generators, wherein the vibrotactile signal has a predetermined vibrotactile profile, wherein the predetermined vibrotactile signal profile has a first vibrotactile profile at a first instance, a second vibrotactile profile at a second instance, and a third vibrotactile profile at a final instance;
wherein the one or more peripheral vibrotactile signal generators are positioned to transmit the vibrotactile signal to acupressure points on the human body,
wherein the handheld and peripheral vibrotactile signal generators include exciter speakers.

15. The apparatus according to claim 14, further comprising a vestibular signal module including one or more mounting zones for suspending the apparatus, each mounting zone having an independent tension force applied thereto for suspending the apparatus.

16. The apparatus according to claim 14, wherein the auditory signal and the vibrotactile signal are synchronous.

* * * * *